United States Patent [19]
Garita

[11] Patent Number: 5,921,255
[45] Date of Patent: Jul. 13, 1999

[54] ORAL CLEANSING ARTICLE AND METHOD OF CLEANING TEETH WITH THE SAME

[76] Inventor: Jose R. Garita, Urb. Los Anonos. #34 San Rafel, Escazu San Jose, Costa Rica

[21] Appl. No.: 08/843,402

[22] Filed: Apr. 15, 1997

[51] Int. Cl.⁶ .................................................. A61C 15/00
[52] U.S. Cl. .......................... 132/329; 132/321; 433/216; 15/167.1; 15/104.93; 119/709
[58] Field of Search ................... 132/321, 329; 119/709, 710; 606/234, 235, 236; 433/216, 229; 601/38; 15/167.1, 104.93

[56] References Cited

U.S. PATENT DOCUMENTS

| | | | |
|---|---|---|---|
| 1,268,470 | 6/1918 | Johnson | 606/235 |
| 2,772,478 | 12/1956 | Halford | 132/321 |
| 3,071,476 | 1/1963 | Werft et al. | 15/167.1 |
| 3,231,925 | 2/1966 | Conder | 15/167.1 |
| 3,587,590 | 6/1971 | Hastings | 606/234 |
| 3,853,412 | 12/1974 | Griffin | 15/104.93 |
| 4,149,815 | 4/1979 | Kawam | 15/104.93 |
| 4,585,416 | 4/1986 | DeNiro et al. | 15/104.93 |
| 4,748,709 | 6/1988 | Oates | 15/104.93 |
| 4,802,444 | 2/1989 | Markham et al. | 119/709 |
| 5,292,336 | 3/1994 | Spence, Jr. et al. | 606/234 |
| 5,595,142 | 1/1997 | Chill | 119/710 |
| 5,647,302 | 7/1997 | Shipp | 119/709 |
| 5,649,964 | 7/1997 | Berman et al. | 606/233 |

FOREIGN PATENT DOCUMENTS

| | | | |
|---|---|---|---|
| MI 76 | 2/1996 | Costa Rica . | |
| 4309935 | 9/1994 | Germany | 433/216 |
| 604677 | 9/1978 | Switzerland | 132/329 |
| 82/02481 | 8/1982 | WIPO | 15/167.1 |

*Primary Examiner*—Todd E. Manahan
*Attorney, Agent, or Firm*—Cushman Darby & Cushman; IP Group of Pillsbury Madison & Sutro LLP

[57] ABSTRACT

An oral hygiene article adapted to be received as a whole within a mouth so that the article can thereby be manipulated with the tongue to dislodge foreign particles, promote salivary excretion, drag bacterial plaque, and massage the gums. The article includes at least a core portion and a plurality of protruding members extending from the core portion. The protruding members each have a proximal end connected to the core portion and a distal end portion opposing the proximal end and spaced from the core portion. One or more of the protruding members has a distal end that terminates in an associated substantially linear edge. One or more of the protruding members can have a polygon-shaped cross section that continuously decreases in area from the proximal end portion to the distal end portion to define the substantially linear edge.

23 Claims, 5 Drawing Sheets

ORAL CLEANSING ARTICLE AND METHOD OF CLEANING TEETH WITH THE SAME

BACKGROUND OF THE INVENTION

1. Field of Invention

The present invention relates generally to an oral cleansing article, and in particular to an oral cleansing article adapted to be received in the mouth as a whole and manipulatable with the tongue to dislodge foreign particles, promote salivary excretion, massage the gums, and drag bacterial plaque.

2. Description of Related Art

Due to increasing demands associated with occupational and social activities, personal commitments to health care, especially preventive health care, often suffer. Simple preventive treatments, such as the brushing and flossing of teeth, often are overlooked, neglected, or consciously deferred until a later, more convenient time. Unfortunately, continued neglect of dental hygiene can detrimentally lead to accumulations of harmful bacterial plaque in the mouth, especially at interfacial boundaries defined between adjacent teeth and between teeth and gums.

It would, therefore, be advantageous to provide a self-supporting oral hygiene article that could be employed concurrently with normal occupational and social activities. Such an article preferentially would be receivable as a whole in the mouth during use and capable of being used involuntarily so that attention could be maintained during occupational and social activities.

An oral cleansing article adapted to be received in a human mouth is disclosed in Costa Rican Patent No. MI 76, patented Feb. 2, 1996, the complete disclosure of which is incorporated herein by reference. The oral cleansing article disclosed in this related art is depicted at FIG. 1 herein and generally designated by reference numeral 100.

As shown in FIG. 1, this conventional article 100 includes a core portion 102 having a plurality of protruding members 104 extending therefrom. The Costa Rican patent discloses that the protruding members 104 are purportedly configured to define complementary shapes with respect to the anatomical structure of the teeth and gums.

Each of the protruding members 104 of the conventional article 100 has a generally conical shape terminating in a generally rounded distal end 108. Although this configuration is purported to complement the shapes of the teeth and gums, the rounded shape of the distal ends 108 prevents the protruding members 104 of the conventional article 100 from advancing deep into the interfacial boundary defined between adjacent teeth or between a tooth and gum of the mouth. Thus, the effectiveness of the conventional article 100 in dislodging foreign particles, such as food particles, embedded in such interfacial boundaries is limited. Moreover, the relatively small surface region defined by the apex of the distal end 108 of protruding members 104 provides an inferior contacting interface between the conventional article and the gums, thereby restricting the massaging function of the protrusion members 104 of the conventional article 100.

A need, therefore, exists to provide an oral cleansing article suitable for dislodging foreign particles embedded in interfacial boundaries defined between adjacent teeth of the mouth or between a tooth and gum of the mouth, while simultaneously providing a large contacting interface for massaging the gums.

SUMMARY OF THE INVENTION

It is, therefore, an object of the present invention to solve the aforementioned problems associated with the related art as well as the need expressed above. In accordance with the principles of the present invention, this objective is obtained by providing an oral hygiene article adapted to be received as a whole within a human mouth. The article comprises a core portion and a plurality of protruding members extending from the core portion. Each of the protruding members has a proximal end connected to the core portion and a distal end portion opposing the proximal end and spaced from the core portion. The distal end of one or more of the protruding members terminates in an associated substantially linear edge.

In accordance with one particular embodiment of the present invention, one or more of the protruding members of the article can have a polygon-shaped cross section that continuously decreases in area from the proximal end portion to the distal end portion and terminates in an associated substantially linear edge at the distal end.

Since the article is adapted to be received as a whole within a mouth, the article can be manipulated by the tongue, lips, and/or cheeks to dislodge foreign particles, promote salivary excretion, and massage the gums. Further, the configuration of the protruding members, and in particular the substantially linear edges of the respective distal end portions, allows the protruding members to advance into and dislodge foreign particles from interfacial boundary regions defined between adjacent teeth of the mouth or between a tooth and gum of the mouth, while simultaneously providing a large contacting interface for massaging the gums. The article also stimulates saliva flow, which increases the pH in the mouth and cleans agglomerates of residual starches from retentive areas in the mouth.

These and other objects, features, and advantages of the present invention will become apparent from the following detailed description when taken in conjunction with the accompanying drawings which illustrate, by way of example, the principles of the present invention.

BRIEF DESCRIPTION OF THE DRAWING

In order that the manner in which the above-recited and other advantages and objects of the invention are obtained may be understood, a more particular description of the invention described above will be rendered by reference to the appended drawings. Understanding that these drawings only provide information concerning exemplary embodiments of the invention and are not therefore to be considered limiting of its scope, the invention will be described and explained with additional specificity and detail through the use of the accompanying drawings, in which.

DESCRIPTION OF THE PREFERRED EMBODIMENTS

A detailed description of the present invention is provided below.

Figure 1:
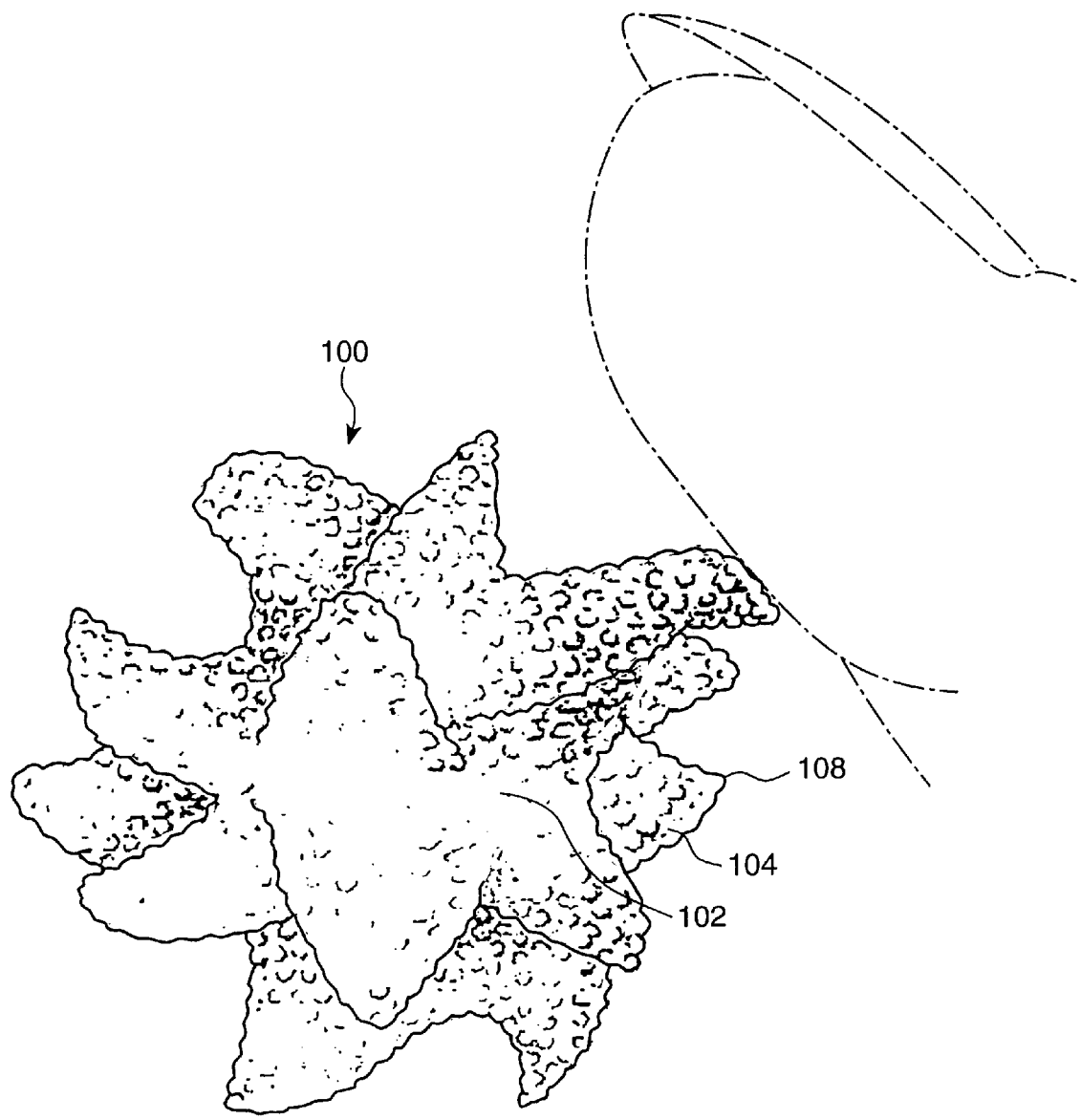
FIG. 1 is a perspective view depicting a conventional oral cleansing article.
Figure 2:
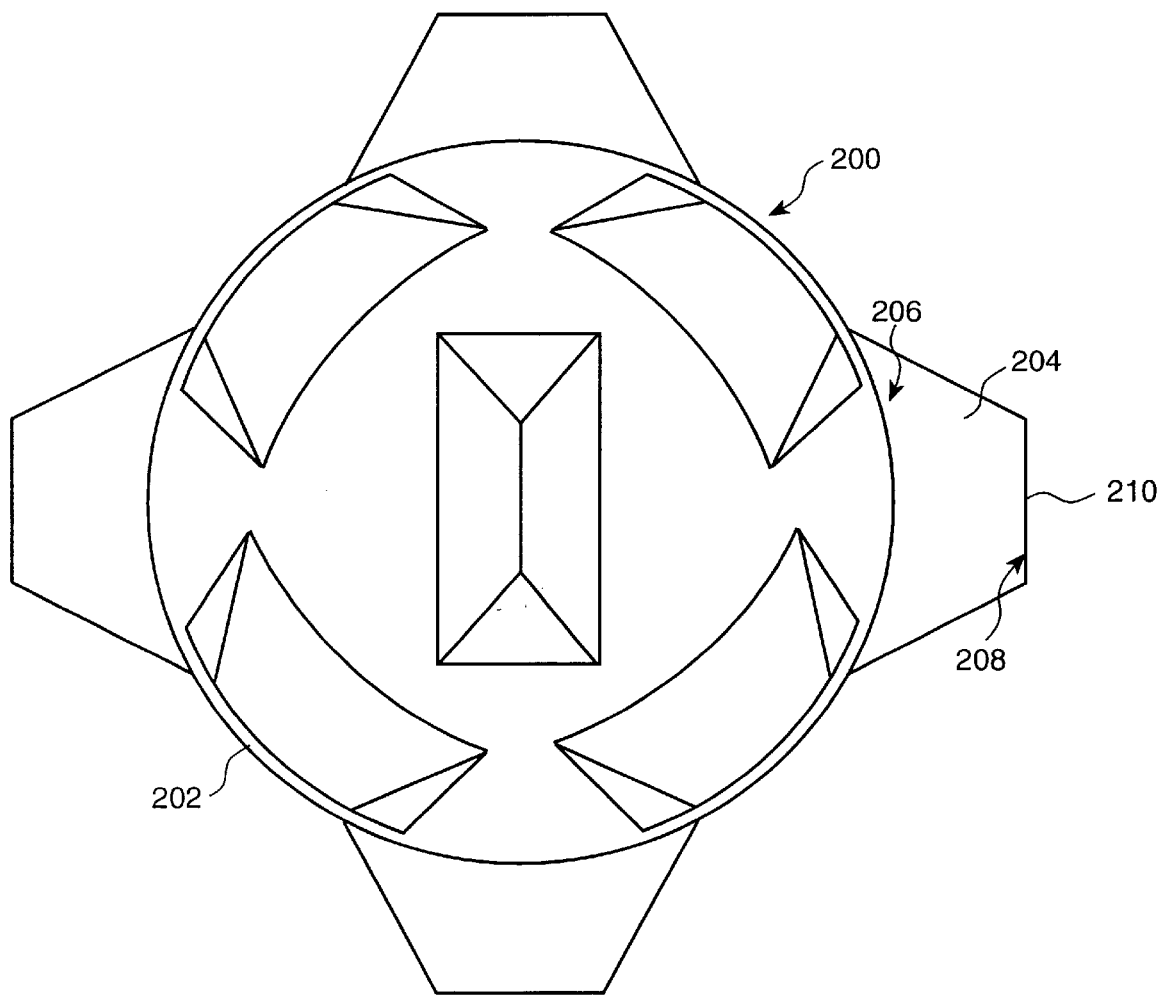
FIG. 2 is a perspective view illustrating an oral cleansing article according to one embodiment of the present invention.

Shown in FIG. 2 is an oral hygiene article, generally designated by reference numeral 200, of appropriate dimension and configuration to be received as a whole within a human mouth, such as the human mouth of an adult or adolescent. The article 200 is defined by at least a core portion, generally designated by reference numeral 202.

Extending from the core portion 202 is a plurality of protruding members 204. Each of the protruding members 204 has a proximal end, generally designated by reference numeral 206, connected to the core portion 202 and a distal end portion, generally designated by reference numeral 208, opposing the proximal end 206 and spaced from the core portion 202. At least one, and preferably all, of the distal end portions 208 terminates in a substantially linear edge 210 or ridge that is resilient in use.

The configurations of the protruding members 204 can vary so long as at least one of the protruding members 204 has a distal end portion 208 that terminates in an associated edge 210 that is substantially linear and resilient. Preferably, the associated linear edge 210 is configured to substantially complement at least a portion of an interfacial boundary defined between adjacent teeth of the mouth or between a tooth and gum of the mouth. As is further depicted in FIG. 2, the protruding members 204 may be spaced apart from each other and dispersed about an outer surface of the core portion 202 by a sufficient distance so that any one of the substantially linear resilient edges 210 is insertable into interfacial boundary regions defined between adjacent teeth or between a tooth and gum without being encumbered by the remaining ones of the substantially linear resilient edges 210.

Exemplary embodiments of protruding members 204 suitable for use in the present invention are illustrated in FIGS. 3A, 3B, 4–8, and 9A–9C and discussed below.

Figure 3A:
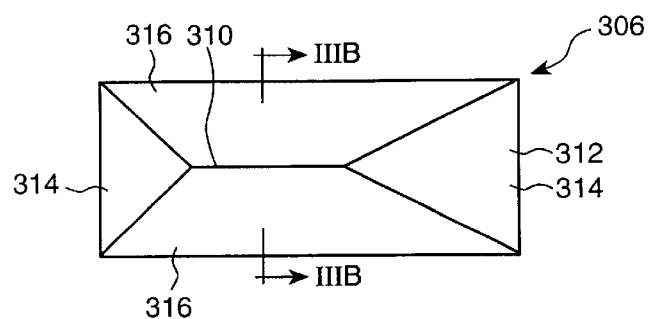
FIG. 3A is an enlarged overhead view of a protruding member suitable for use as part of the oral cleansing article of FIG. 2.
Figure 3B:
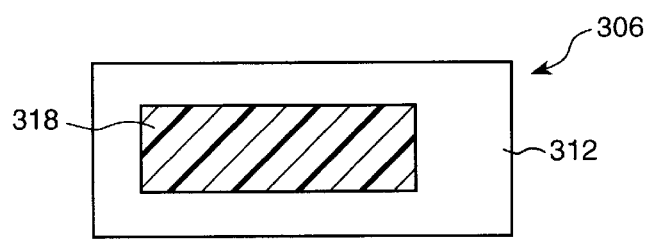
FIG. 3B is an enlarged cross-sectional view taken along sectional line IIIB—IIIB of the protruding member shown in FIG. 3A.

FIG. 3A illustrates a protruding member, generally designated by reference numeral 306, defined by a generally pyramidal shape with a rectangular base 312, opposing triangular facial ends 314 arranged in a non-parallel relationship and at an oblique angle with respect to the base 312, and opposing trapezoidal facial sides 316 extending from opposite ends (unnumbered) of the base 312 and intersecting each other and terminating in a linear edge 310. The protruding member 306 has polygon-shaped cross sections, one of which is illustrated in FIG. 3B and designated by reference numeral 318, that continuously decrease in area from the proximal end portion 306 to the distal end portion 308 of the protruding member 304.

Figure 4:
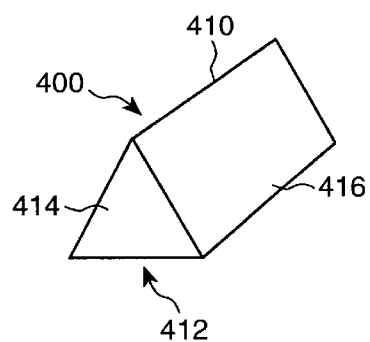
FIG. 4 is a perspective view illustrating a second embodiment of a protruding member suitable for use in the oral cleansing article of the present invention.

In accordance with a second embodiment illustrated in FIG. 4, a protruding member 400 is provided having opposing triangular facial ends 414 arranged parallel with respect to one another and in transverse relationship with respect to the base 412. Opposing rectangular facial sides 416 extend from opposite ends of the base 412 and intersect and terminate in a linear edge 410 spaced from the base 412. The resultant protruding member 400 possesses the elongated triangular configuration shown in FIG. 4.

Figure 5:
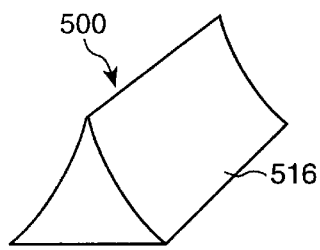
FIG. 5 is a perspective view illustrating a third embodiment of a protruding member suitable for use in the oral cleansing article of the present invention.
Figure 6:
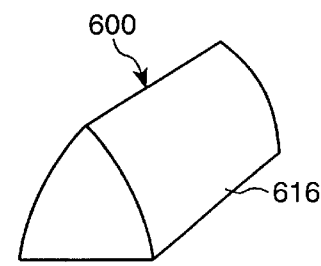
FIG. 6 is a perspective view illustrating a fourth embodiment of a protruding member suitable for use in the oral cleansing article of the present invention.

In accordance with third and fourth embodiments of the present invention illustrated in FIG. 5 and FIG. 6, respectively, protruding members 500 and 600 can have opposing quadrilateral facial sides 516 and 616 that are curved towards or away from each other.

Figure 7:
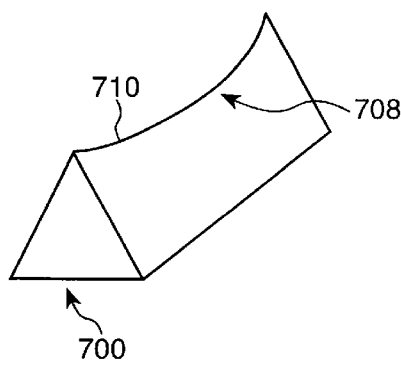
FIG. 7 is a perspective view illustrating a fifth embodiment of a protruding member suitable for use in the oral cleansing article of the present invention.
Figure 8:
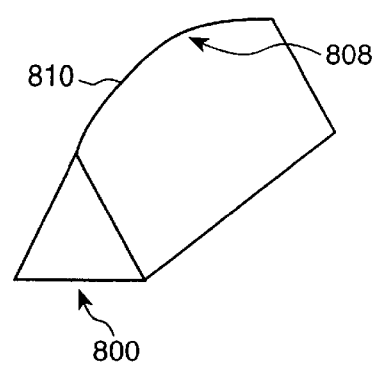
FIG. 8 is a perspective view illustrating a sixth embodiment of a protruding member suitable for use in the oral cleansing article of the present invention.

FIG. 7 illustrates a fifth embodiment in which a protruding member 700 with a concave distal end portion, generally designated by reference numeral 708, terminates in a curvilinear edge 710 or ridge. Conversely, FIG. 8 illustrates a sixth embodiment in which a protruding member 800 with a convex distal end portion, generally designated by reference numeral 808, terminates in a curvilinear edge 810 or ridge.

Figure 9A:
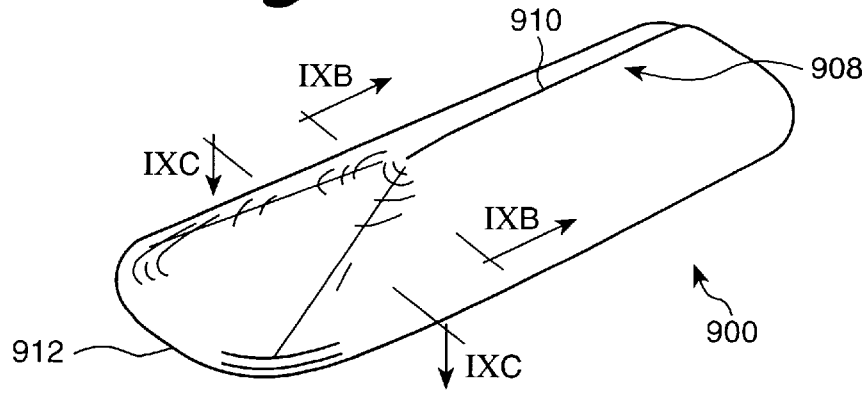
FIG. 9A is a perspective view illustrating a seventh embodiment of a protruding member suitable for use in the oral cleansing article of the present invention.
Figure 9B:
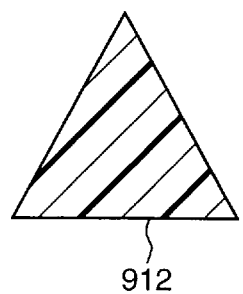
FIG. 9B is a sectional end view of the protruding member of FIG. 9A taken along sectional line IXB—IXB.
Figure 9C:
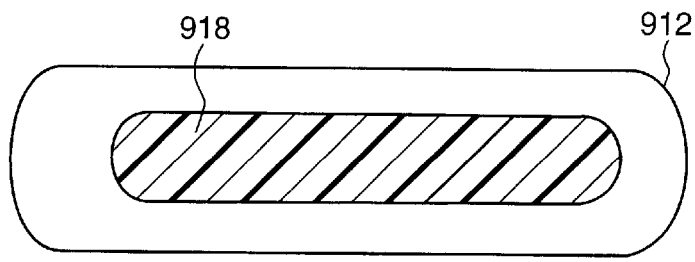
FIG. 9C is a sectional top view of the protruding member of FIG. 9A taken along sectional line IXC—IXC.

FIGS. 9A–9C illustrate still another embodiment of the present invention, in which a protruding member 900 has rounded sides. As shown by the sectional view of FIG. 9C, the protruding members 900 are defined by an elongated oval base 912 and cross sections, one of which is illustrated in FIG. 9C and designated by reference numeral 918. As in the other embodiments, the protruding member 900 has a distal end portion, generally designated by reference numeral 908, that terminates in a substantially linear edge 910 or ridge that is resilient.

It should be understood that the article of the present invention can intermix two or more of the foregoing or other embodiments, so that protruding members having varying configurations extend from a common core portion. In this manner, the article is provided with several different substantially linear edge or ridge portions. Consequently, in use the article can be adjusted in orientation by the user to apply the edge or ridge portion to a desired region of the mouth to be treated so that the edge or ridge portion selected most closely complements that desired region.

Preferably, the article contains 8 to 12 protruding members, with at least two and more (preferably each) of the protruding members terminating in a substantially linear edge that is resilient. The protruding members can be spaced apart from each other and dispersed about the outer surface of the core portion.

In its broadest aspects, several variations and modifications to the above-discussed article can be implemented without departing from the scope of the present invention. For example, as depicted in FIG. 2, the core portion 202 has a spherical configuration; however, it should be understood that the configuration of the core portion 202 is not so limited. Instead, the core portion 202 can have a block, polygonal, or indistinct configuration.

In addition, although the entire article 200 (including its core portion 202, protruding members 204, and distal end portion 208) is preferably made of a polymeric or similar material that is resilient and durable, the present invention is not so limited. For example, the core portion 202 and any portion of the protruding member 204 (other than the distal end portion 208 of at least one protruding member) can optionally be formed of a nonresilient malleable material that deforms during use so that the configuration of the core portion 202 undergoes change during use. In addition, flavoring can optionally be added to the material forming the article 200 to improve its receptiveness by the user.

Figure 10A:
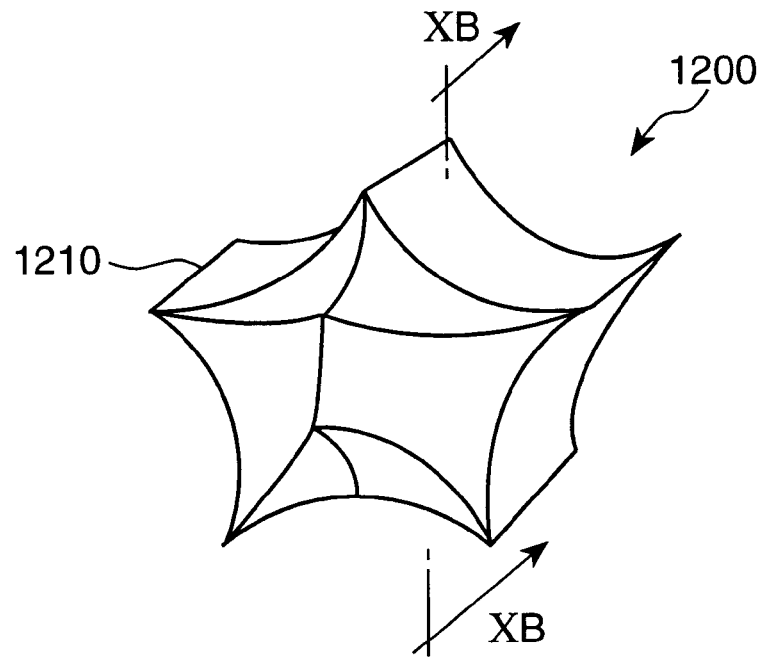
FIG. 10A is a perspective view illustrating an oral cleansing article according to another embodiment of the present invention.
Figure 10B:
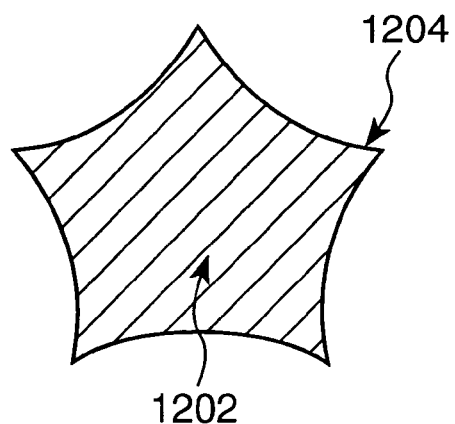
FIG. 10B is a sectional view taken along sectional line XB—XB of FIG. 10A.

With reference to FIGS. 10A and 10B, there is shown an alternative embodiment of the present invention. In order to facilitate an understanding of the structure and operation of this embodiment, and in the interest of brevity, the structural elements of the embodiments of FIGS. 10A and 10B corresponding in structure or function with elements of the embodiment in FIG. 2 have been designated by the same reference numerals used in designating the corresponding element of the embodiment of FIG. 2 with the addition of the prefix numeral 1000.

In FIGS. 10A and 10B, an oral hygiene article, generally designated by reference numeral 1200, is provided having appropriate dimension and structure to be received as a whole within a human mouth. The article 1200 is defined by at least a core portion, generally designated by reference numeral 1202.

Integrally formed with and extending from the core portion 1202 is a plurality of protruding members 1204. The protruding members 1204 each have a proximal end integrally connected to the core portion 1202 and a distal end portion opposing the proximal end and spaced from the core portion 1202. At least one, and preferably all, of the distal end portions terminates in a substantially linear edge 1210 or ridge that is resilient. As shown in FIG. 10B, the interfacial boundary between the core portion 1202 and protruding members 1204 integrally connected thereto is indiscriminate.

Although the present invention has been described in detail with reference to its presently preferred embodiments, it will be understood by those of ordinary skill in the art that various other modifications and improvements to the present invention are believed to be apparent to one skilled in the art. All such modifications and improvements are intended to be included within the scope of the appended claims.

What is claimed is:

1. An oral hygiene article receivable as a whole within a human mouth, said article comprising:
    a spherical core portion; and
    a plurality of protruding members having respective proximal ends which contact said core portion and extending to respective distal end portions,
    at least one of said distal end portions terminating in a substantially linear resilient edge.

2. An oral hygiene article according to claim 1, wherein at least two of said distal end portions terminate at respective associated linear resilient edges.

3. An oral hygiene article according to claim 1, wherein each of said distal end portions terminate at respective associated linear resilient edges.

4. An oral hygiene article according to claim 1, wherein said distal end portions terminate at respective associated linear resilient edges configured to substantially complement at least a portion of an interfacial boundary defined between adjacent teeth of the mouth or between a tooth and gum of the mouth.

5. An oral hygiene article according to claim 4, wherein said protruding members are spaced apart from each other and dispersed about an outer surface of said core portion by a sufficient distance so that any one of said substantially linear resilient edges is insertable into interfacial boundary regions defined between adjacent teeth of the mouth or between a tooth and gum of the mouth without being encumbered by the remaining ones of said substantially linear resilient edges.

6. An oral hygiene article according to claim 4, wherein said plurality of protruding members includes at least eight and no more than twelve protruding members.

7. An oral hygiene article according to claim 6, wherein said plurality of protruding members includes first and second protruding members having different sizes from each other.

8. An oral hygiene article according to claim 1, wherein said protruding members are spaced apart from each other by a sufficient distance so that said substantially linear resilient edge is insertable into interfacial boundary regions defined between adjacent teeth of the mouth or between a tooth and gum of the mouth without being encumbered by the remaining ones of said protruding members.

9. An oral hygiene article according to claim 1, wherein said edge is linear.

10. An oral hygiene article according to claim 1, wherein said edge is curvilinear.

11. An oral hygiene article according to claim 1, wherein said article is prepared from a polymeric material.

12. An oral hygiene article according to claim 1, wherein said protruding members are integrally connected to said core portion.

13. A process for dislodging foreign particles, promoting salivary excretion, dragging bacterial plaque, and massaging gums, said process comprising:
    providing an oral hygiene article receivable as a whole within a human mouth, the article comprising a spherical core portion and a plurality of protruding members having respective proximal ends which contact said core portion and extending to respective distal end portions, at least one of the distal end portions terminating in a substantially linear resilient edges; and
    introducing the oral hygiene article into a human mouth and manipulating the oral hygiene article with the tongue to insert said linear edge into interfacial boundary regions defined between adjacent teeth of the mouth or between a tooth and gum of the mouth while simultaneously massaging the gums.

14. A process according to claim 13, wherein the distal end portions terminate at respective associated linear resilient edges.

15. A process according to claims 14, wherein said protruding members are spaced apart from each other and dispersed about an outer surface of said core portion by a sufficient distance so that any one of said substantially linear resilient edges is insertable into interfacial boundary regions defined between adjacent teeth of the mouth or between a tooth and gum of the mouth without being encumbered by the remaining ones of said substantially linear resilient edges.

16. A process according to claim 12, wherein at least one of the protruding members has a polygon-shaped cross section that continuously decreases in area from the proximal end portion to the distal end portion to thereby terminate in an associated substantially linear edge.

17. A process according to claim 13, wherein the protruding members have respective polygon-shaped cross sections that continuously decrease in area from the respective proximal end portions to the respective distal end portions to thereby terminate at respective associated substantially linear resilient edges.

18. A process according to claim 12, wherein the protruding members are integrally connected to the core portion.

19. A process according to claim 13, wherein said protruding members are spaced apart from each other by a sufficient distance so that said substantially linear resilient edge is insertable into interfacial boundary regions defined between adjacent teeth of the mouth or between a tooth and gum of the mouth without being encumbered by the remaining ones of said protruding members.

20. An oral hygiene article receivable as a whole within a human mouth, said article comprising:

a core portion; and a plurality of protruding members having respective proximal ends which contact said core portion and extending to and terminating at respective distal end portions having respective substantially linear resilient edges, wherein said protruding members are spaced apart from each other and dispersed about an outer surface of said core portion by a sufficient distance so that any one of said substantially linear resilient edges is insertable into interfacial boundary regions defined between adjacent teeth of the mouth or between a tooth and gum of the mouth without being encumbered by remaning ones of said substantially linear resilient edges.

21. An oral hygiene article according to claim 20, wherein said plurality of protruding members includes first and second protruding members having different sizes from each other.

22. An oral hygiene article according to claim 20, wherein said edges are linear.

23. An oral hygiene article according to claim 21, wherein said edges are curvilinear.

\* \* \* \* \*